(12) United States Patent
Kim et al.

(10) Patent No.: US 10,045,843 B2
(45) Date of Patent: Aug. 14, 2018

(54) STRETCHABLE ELECTRONICS FOR ARTIFICIAL SKIN

(71) Applicants: SEOUL NATIONAL UNIVERSITY R&DB FOUNDATION, Seoul (KR); INSTITUTE FOR BASIC SCIENCE, Daejeon (KR)

(72) Inventors: Daehyeong Kim, Incheon (KR); Taeghwan Hyeon, Seoul (KR); Jaemin Kim, Seoul (KR); Mincheol Lee, Gyeongsan-si (KR); Hyungjoon Shim, Seoul (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 174 days.

(21) Appl. No.: 15/055,492

(22) Filed: Feb. 26, 2016

(65) Prior Publication Data

US 2016/0250015 A1 Sep. 1, 2016

(30) Foreign Application Priority Data

Feb. 27, 2015 (KR) .................. 10-2015-0028507

(51) Int. Cl.
| | | |
|---|---|---|
| *A61F 2/10* | (2006.01) | |
| *A61F 2/76* | (2006.01) | |
| *G01L 5/22* | (2006.01) | |
| *A61F 2/50* | (2006.01) | |
| *A61F 2/58* | (2006.01) | |

(52) U.S. Cl.
CPC .............. *A61F 2/105* (2013.01); *A61F 2/50* (2013.01); *A61F 2/76* (2013.01); *G01L 5/228* (2013.01); *A61F 2/583* (2013.01); *A61F 2/586* (2013.01); *A61F 2002/5001* (2013.01); *A61F 2002/5058* (2013.01); *A61F 2002/5061* (2013.01); *A61F 2002/5063* (2013.01); *A61F 2002/766* (2013.01); *A61F 2002/7635* (2013.01); *A61F 2002/7665* (2013.01); *A61F 2250/0096* (2013.01)

(58) Field of Classification Search
CPC ...... A61F 2002/5058; A61F 2002/5059; A61F 2002/5061; A61F 2002/5063; A61F 2002/7765; A61F 2002/766; A61F 2002/7635; A61F 2002/6837; A61B 5/6802
See application file for complete search history.

(56) References Cited

U.S. PATENT DOCUMENTS

2013/0333094 A1* 12/2013 Rogers ................ A41D 19/015
2/161.7

FOREIGN PATENT DOCUMENTS

| JP | 2013514146 A | 4/2013 |
|---|---|---|
| KR | 20150004819 A | 1/2015 |

(Continued)

*Primary Examiner* — Thomas J Sweet
*Assistant Examiner* — Daniel Bissing
(74) *Attorney, Agent, or Firm* — Renaissance IP Law Group LLP

(57) ABSTRACT

A stretchable electronic device for artificial skin and a method of manufacturing the same are disclosed. The stretchable electronic device for artificial skin includes a first encapsulation layer, a heater disposed on the first encapsulation layer, a second encapsulation layer disposed on the heater, a first sensor array layer disposed on the second encapsulation layer, and a third encapsulation layer disposed on the first sensor array layer.

15 Claims, 24 Drawing Sheets

(56) References Cited

FOREIGN PATENT DOCUMENTS

WO     2011084450 A1    7/2011
WO     2013149181 A1    10/2013

\* cited by examiner

Strain Sensor

Temperature Sensor

STRETCHABLE ELECTRONICS FOR ARTIFICIAL SKIN

BACKGROUND OF THE INVENTION

1. Field of the Invention

The present invention relates to a stretchable electronic device for artificial skin and a method of manufacturing the same.

2. Description of the Related Art

Skin-based mechanoreceptors and thermo-receptors gather a large quantity of information from the external environment. The central and autonomic nervous systems analyze such sensory input and transform the input into regulated physiological response and motor output.

Although there has been significant progress in understanding neural circuits for mechanical and thermal sensation, it is very difficult to replicate these capabilities in artificial skin. Thus, many amputees wear prosthetic limbs for cosmetic purposes or as supplementary movement aids rather than as a functional replacement for natural limbs.

Recent advancements in the design of prosthetic limbs integrated with rigid and/or semi-flexible tactile sensors provide sensory reception to enable feedback in response to variable environments. However, there still exists a mechanical mismatch between soft biological tissue and the conventional electronic device in wearable artificial skin, and thus the utility and performance of artificial skin in amputees are limited.

Many attempts have been made to reduce the technological gap between artificial skin and real skin. In this regard, research is ongoing into flexible and/or stretchable tactile sensors based on various micro/nano materials and structures.

Specifically, pressure-sensitive rubber (PSR), which is used as a resistive element that responds to tensile strain, may be integrated with flexible organic electronic devices and nanomaterial-based (nanowire or nanotube) transistors.

However, conventional PSR has a slow response time and undergoes significant hysteresis. A single crystalline silicon-based device provides a rapid response time, but the heterogeneity of geometry and strain profiles of the skin across different anatomies dictates that custom designs be provided for specific body locations.

Accordingly, the heterogeneous integration of pressure, temperature and humidity sensing coupled with electroresistive thermal actuation in site-specific geometrical layouts provides opportunities to drastically advance techniques in smart prosthetics and artificial skin.

SUMMARY OF THE INVENTION

Therefore, the present invention is intended to provide a stretchable electronic device for artificial skin.

In addition, the present invention is intended to provide a method of manufacturing a stretchable electronic device for artificial skin.

An embodiment of the present invention provides a stretchable electronic device for artificial skin, comprising: a first encapsulation layer; a heater disposed on the first encapsulation layer; a second encapsulation layer disposed on the heater; a first sensor array layer disposed on the second encapsulation layer; and a third encapsulation layer disposed on the first sensor array layer.

The first sensor array layer may include at least one selected from among a strain sensor, a pressure sensor, and a temperature sensor.

The first sensor array layer may include a first passivation layer, a semiconductor pattern disposed on the first passivation layer, a first metal pattern disposed on the semiconductor pattern, and a second passivation layer disposed on the first metal pattern.

The semiconductor pattern and the first metal pattern may have a serpentine shape. The semiconductor pattern may be a silicon pattern formed by patterning a doped silicon nanomembrane. The semiconductor pattern may be a silicon nanoribbon.

The pressure sensor may have a cavity in the first passivation layer to expose the semiconductor pattern The strain sensor and the pressure sensor may have different curvatures depending on the position of the human body to which the stretchable electronic device is attached, and the strain induced by the human body may be further relieved with an increase in the curvature.

The strain sensor may have a Wheatstone bridge configuration.

The divergence between I-V curves of the temperature sensor may be decreased under different strains, with an increase in the curvature of the temperature sensor.

The heater may include a third passivation layer, a second metal pattern disposed on the third passivation layer, and a fourth passivation layer disposed on the second metal pattern.

The second metal pattern may have a serpentine shape.

The stretchable electronic device may further comprise a second sensor array layer disposed on the third encapsulation layer.

The second sensor array layer may include a humidity sensor.

The humidity sensor may include a fifth passivation layer, a third metal pattern disposed on the fifth passivation layer, and a sixth passivation layer disposed on the third metal pattern.

The third metal pattern may have a serpentine shape.

The humidity sensor may detect a change in capacitance induced by a change in the permittivity of the sixth passivation layer, into which water molecules are absorbed.

The first encapsulation layer, the second encapsulation layer, and the third encapsulation layer may each be formed of a silicone polymer or silicone rubber. The silicone polymer may be polydimethylsiloxane (PDMS).

In an exemplary embodiment, the strain sensor may be a p-type doped silicon nanoribbon and may measure the applied strain based on the piezoelectric characteristics of the silicon nanoribbon. The upper and lower surfaces of the silicone nanoribbon may be encapsulated with a polyimide layer having a thickness of 1 μm and the silicon nanoribbon may form a neutral mechanical plane.

In an exemplary embodiment, the pressure sensor may be a p-type doped silicon nanoribbon and may measure the applied strain based on the piezoelectric characteristics of the silicon nanoribbon. The upper surface of the silicon nanoribbon may be encapsulated with a polyimide layer having a thickness of 1 μm.

In an exemplary embodiment, the temperature sensor may be a p-n-type doped silicon nanoribbon and may measure the external temperature depending on the temperature characteristics of the diode in the p-n-type doped silicon nanoribbon. The upper and lower surfaces of a p-n-type doped silicon nanoribbon may be encapsulated with a polyimide layer and the silicon nanoribbon may form a neutral mechanical plane.

In an exemplary embodiment, the humidity sensor may be a patterned metal line and may measure changes in capacitance between the polyimide layer and the metal that depend on humidity, thereby determining the humidity. The patterned metal line may be encapsulated with a polyimide layer having a thickness of 1 μm.

Another embodiment of the present invention provides a method of manufacturing a stretchable electronic device for artificial skin, comprising: (i) coating a silicon oxide wafer with polyimide, (ii) transferring a doped silicon nanomembrane (SiNM) onto the polyimide and curing it, (iii) patterning the SiNM to form a silicon nanoribbon (SiNR), (iv) depositing a metal and patterning it, (v) performing encapsulation with polyimide and curing, (vi) etching the polyimide, thus obtaining a device, (vii) removing the device from the silicon oxide wafer and transferring it onto a PVA film coated with PDMS, and (viii) performing encapsulation with PDMS.

In an exemplary embodiment, in the step (i), the silicon oxide wafer may be spin-coated (8000 rpm, 60 sec) with polyamic acid.

In an exemplary embodiment, in the step (ii), the doped silicon nanomembrane may be transferred onto the spin-coated wafer using a transfer printing process and then a polyimide layer may be formed by curing the polyamic acid layer at 250° C. for 1 hr.

In an exemplary embodiment, in the step (iii), a silicon nanoribbon (SiNR) may be formed by patterning the transferred SiNM through photolithography.

In an exemplary embodiment, in the step (iv), the metal may be deposited to a thickness of about 100 μm using a vacuum thermal deposition process and thus may be patterned through photolithography and wet etching.

In an exemplary embodiment, in the step (v), a polyimide encapsulation layer may be formed by spin-coating (8000 rpm, 60 sec) using polyamic acid as in the step (i) and then curing at 250° C. for about 1 hr.

In an exemplary embodiment, in the step (vi), the polyimide may be etched through photolithography and reactive ion etching.

In an exemplary embodiment, in the step (vii), the device may be transferred onto the PVA film, spin-coated (3000 rpm, 30 sec) with PDMS (40:1, PDMS:curing agent w/w), through a transfer printing process using water soluble tape.

In an exemplary embodiment, in the step (viii), the encapsulation may be performed with PDMS (40:1, PDMS:curing agent w/w) through spin coating (3000 rpm, 30 sec).

According to the present invention, the stretchable electronic device for artificial skin can exhibit outstanding spatiotemporal sensitivity and mechanical reliability, and can thus respond to a variety of external environments and stimuli, thereby significantly improving the sensing capability of the artificial skin.

BRIEF DESCRIPTION OF THE DRAWINGS

The above and other objects, features and advantages of the present invention will be more clearly understood from the following detailed description taken in conjunction with the accompanying drawings, in which:

FIGS. 8A to 8C illustrate the results of evaluation of strain of the knee during the bending motion, wherein FIG. 8A illustrates the regional strain maps for the skin of the knee calculated using the positional information obtained by the motion-capture system upon minimum bending (on the left) and maximum bending (on the right) (in which the insets show the knee having the reflective markers attached thereto), FIG. 8B illustrates an enlarged image of the strain gauge array attached completely to the bent knee, and FIG. 8C illustrates the percent resistance changes for the strain gauges in different designs (S1, S2, S3), depending on the motion state (repeated relaxation and bending of the knee) (in which S1 and S2 designs become disordered during the repeated bending motion);

DESCRIPTION OF SPECIFIC EMBODIMENTS

Figure 1A:
FIG. 1A is an image illustrating the artificial skin according to an embodiment of the present invention, having integrated stretchable sensors and actuators covering the entire surface of a prosthetic hand (in which the inset shows the artificial skin stretched about 20%)

Hereinafter, a detailed description will be given of embodiments of the present invention. The present invention is not limited to the embodiments disclosed herein, but may be modified into different forms. These embodiments are provided to thoroughly explain the disclosure and to sufficiently transfer the spirit of the present invention to those skilled in the art. Thus, such embodiments are not set forth to be construed as limiting the present invention.

Although terms such as "first", "second", etc. are used to describe various elements, the elements should not be limited by such terms. These terms are merely used to distinguish the elements from each other. Also, when a first element is described as being disposed on a second element, it means that the first element may be directly formed on the second element, or a third element may be interposed between the first and the second element.

Throughout the drawings, the sizes of the elements or relative sizes of the elements may be exaggeratedly depicted to provide an easily understood description of the present invention. Furthermore, the shapes of the elements shown in the drawings may be slightly altered due to changes in the manufacturing process. Therefore, it should be understood that the embodiments of the present invention are not limited only to the shapes depicted in the drawings, unless otherwise stated, and that some modifications may be incorporated therein.

Manufacture of SiNR-Based Device

Doping of a silicon-on-insulator (SOI) wafer is first performed using a spin-on-dopant (SOD). The doped portion is transfer-printed onto a polyimide (PI) film, which is applied on a silicon oxide ($SiO_2$) wafer. Using photolithography and reactive ion etching, SiNR is additionally patterned. Thermal evaporation for metal deposition (Au/Cr, 70 nm/7 nm), photolithography and wet-etching steps are carried out, thus forming serpentine metal lines. The upper PI layer is spin-coated, and a total of three layers (PI/device/PI) are patterned by reactive ion etching. The resulting device is transfer-printed onto PDMS, applied through spin coating on a PVA film, and encapsulated by another PDMS via spin coating. In order to attach the device to the target substrate (e.g. a prosthetic hand), the encapsulated device is attached to the target position and then the PVA film is removed through immersion in deionized water.

Manufacture of Au-Based Device

A PI precursor solution is applied through spin coating on a $SiO_2$ wafer. The PI layer is sufficiently cured at 250° C. for 1 hr. In order to form separate electrodes for a humidity sensor and resistive conduction paths for a heater, Au/Cr (70 nm/7 nm) layers are deposited using a thermal evaporation process. The deposited metal film is patterned through photolithography. For the encapsulation, another PI layer is applied through spin coating and cured using the same procedures and conditions. The whole structure (PI/metal/PI) is patterned in stretchable form, separated from the $SiO_2$ wafer, and then transferred to the polymer substrate in the same manner as the SiNR-based device.

Artificial Skin Having Site-Specifically Designed Stretchable Electronic Device

Figure 1B:
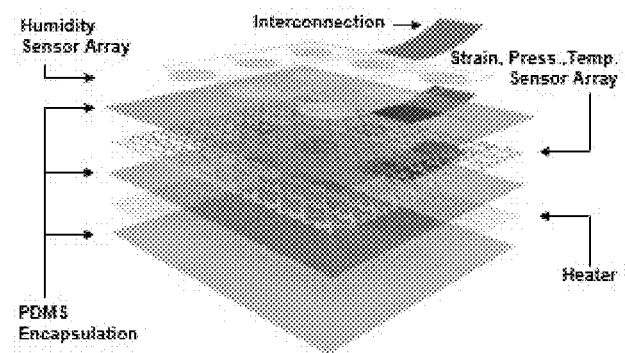
FIG. 1B is an exploded perspective view illustrating the artificial skin comprising six stacked layers.
Figure 1C:
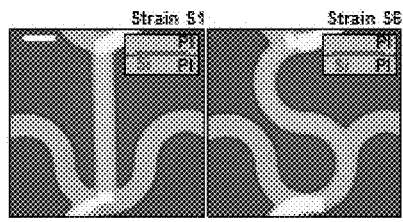
FIG. 1C illustrates representative microscope images of the SiNR strain gauges (in which S1 on the left has a curvature of 0 mm$^{-1}$ and S6 on the right has a curvature of 10 mm$^{-1}$)

FIG. 1A illustrates an image of artificial skin having an integrated electronic device laminated on the surface of a prosthetic hand. The surface of the artificial skin is highly compliant, and is mechanically coupled to the curvilinear surface of the prosthetic hand. The stacked layers (FIG. 1B) represent the locations of the embedded electronic devices, sensors, and actuators, and the enlarged views thereof are illustrated in FIGS. 1C to 1F.

The bottom layer includes an electroresistive heater in a filament pattern bonded to polydimethylsiloxane (PDMS). The thermal actuator is in a fractal-inspired format (FIG. 1F) to facilitate uniform heating during stretching and contraction of the skin layer. In order to monitor tactile and thermal feedback during actuation, the strain sensor (FIG. 1C), pressure sensor (on the left of FIG. 1D) and temperature sensor (on the right of FIG. 1D) arrays are used in the middle layer of the stack. The network of the sensors has spatially varying geometrical designs, ranging from linear to serpentine shapes (S1 to S6 of FIGS. 2A and 2B), depending on the mechanics of the underlying prosthetic hand. A humidity sensor array, comprising the coplanar capacitors (FIG. 1E) in the upper encapsulation layer, detects changes in capacitance at different humidity levels (in which the bottom right inset of FIG. 1E shows the enlarged view) to acquire information about ambient conditions.

All of the aforementioned devices include ultrathin regions, that is, SiNR (silicon nanoribbon) or gold (Au) NR, which are passivated by PI (the top right insets of FIGS. 1C to 1F). The tactile pressure sensor may include a cavity for enhancing sensitivity in response to mechanical pressure changes. The important material utilized in the manufacture of such a tactile sensor is p-type doped single crystalline SiNR, which has both high piezoresistivity (gauge factor: about 200) and low fracture toughness (about 1.0 MPa m$^{1/2}$). In order to prevent mechanical defects, ultrathin (about 110 nm) SiNR is disposed in the neutral mechanical plane of the stack. FIG. 1G is an SEM image of a crack-free SiNR transferred onto the silicon oxide substrate. The SiNR is ultrathin and exhibits sufficient mechanical flexibility to endure mechanical deformation such as wrinkles (FIG. 1H). FIG. 1I illustrates a cross-sectional TEM image of the SiNR located in the neutral mechanical plane (PI/SiNR/PI structure). These designs may minimize bending-induced strain.

Detection of Regional Strain of Skin in Various Motions

The skin typically experiences multi-axial forces and undergoes a variety of angular and linear motions at different body locations. This heterogeneity in movement and strain of the skin requires location-specific optimization of sensors and actuators in artificial skin and prosthetics.

Figure 3A:
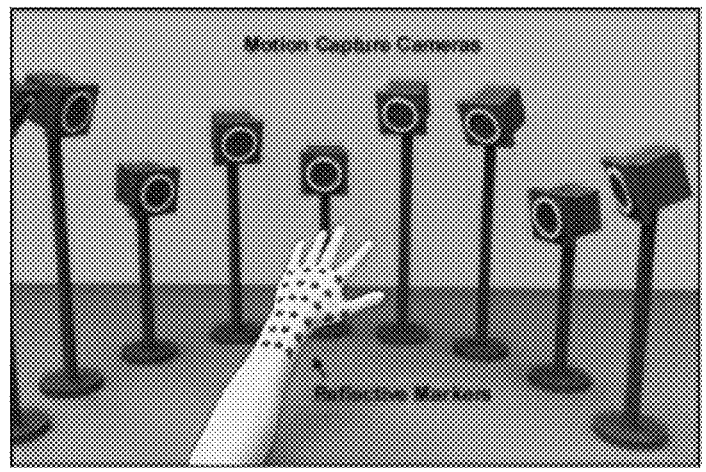
FIG. 3A illustrates the motion-capture system according to the present invention.
Figure 3B:
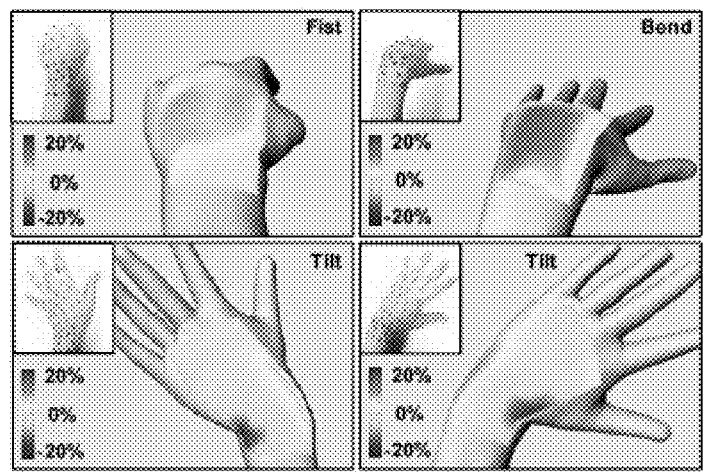
FIG. 3B illustrates regional strain maps of the skin, calculated using positional information acquired by the motion-capture system for four different motions: fist clenching, bending forward, tilting left and right (the top left inset of each of which shows the actual hand with reflective markers)
Figure 4:
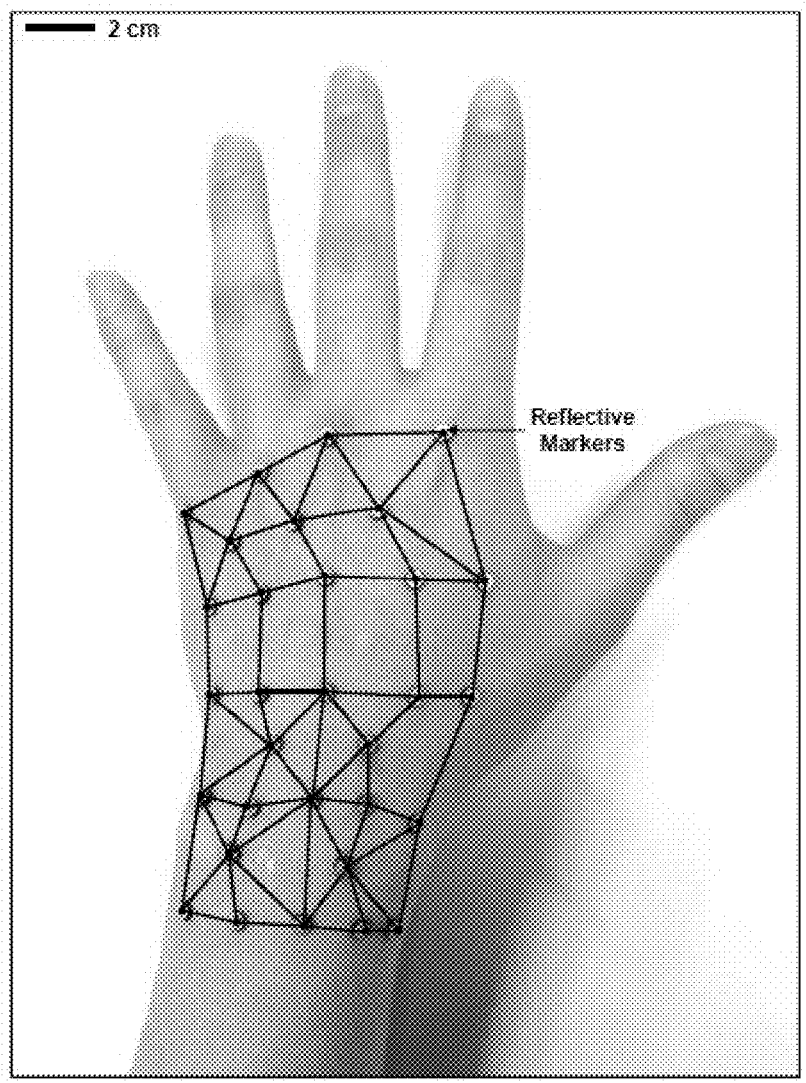
FIG. 4 illustrates reflective markers for measuring the deformation of the skin of the hand using the motion-capture system, the lines of which indicate the distances between the adjacent markers to calculate the induced strain.

To characterize the mechanical behavior of movement and skin mechanics on the arm and the hand, movement and strain are acquired from several target points (FIG. 4) on the skin using the motion-capture camera system (FIG. 3A). Specifically, 12 motion-capture cameras are synchronously used to acquire three-dimensional coordinates of reflective markers attached to the hand and the wrist. Four representative hand movements, including fist clenching as well as vertical (bending) and lateral (tilting) wrist movements, are analyzed (FIG. 3B). Also, the strain distribution is calculated by measuring displacement relative to neighboring reflective markers. During fist clenching, the skin is stretched about 5% (on the top left of FIG. 3B), whereas significantly greater strain (about 16%) is induced in response to bending (on the top right of FIG. 3B). The tilting movement induces compression on the wrinkled side of the wrist, while the skin experiences stretching on the opposite side of the wrist (on the bottom of FIG. 3B).

Figure 3C:
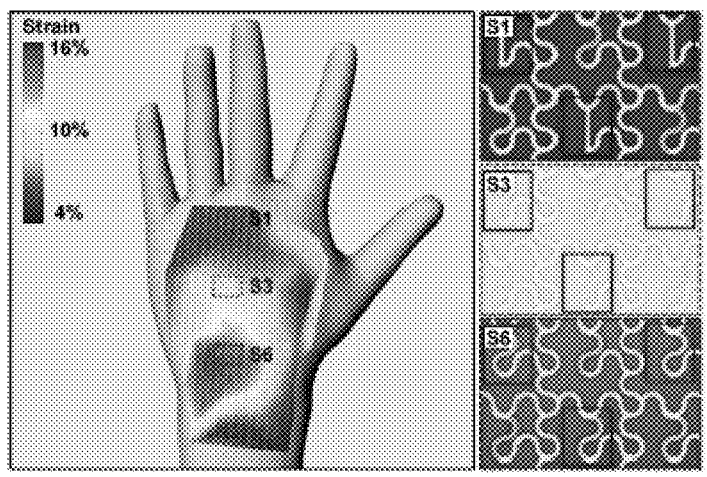
FIG. 3C illustrates the map of maximum stretching range for the entire area, acquired by combining the data results obtained from FIG. 3B, and the corresponding arrangement of the SiNR strain gauge (in which the frames on the right are enlarged views of individual designs (S1, S3 and S6 designs; indicated with black boxes)
Figure 3D:
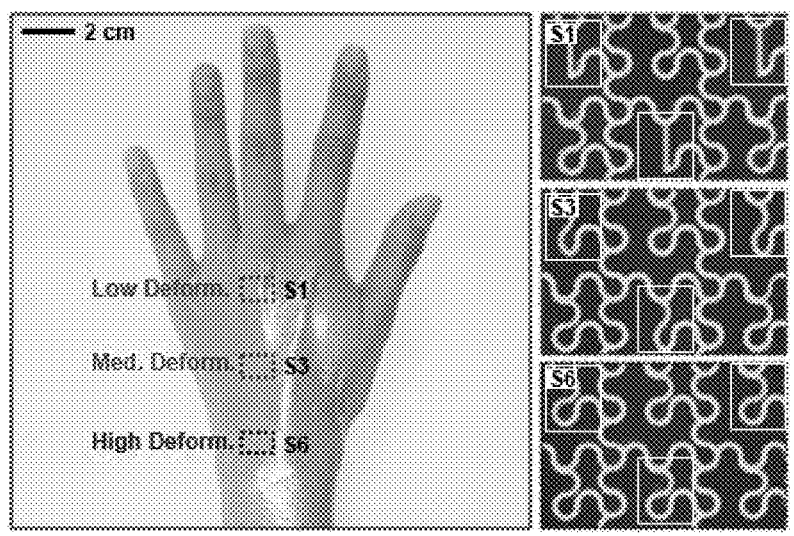
FIG. 3D is a image illustrating the SiNR strain gauge array, conformally attached to the back of the hand (in which the frames on the right are enlarged views of individual designs (indicated with white boxes), and S1, S3 and S6 designs correspond to low, medium and high deformation locations, respectively)

By gathering such movement data, strain profiles near the wrist and the hand are mapped (FIG. 3C). For regions where the skin is hardly stretched, linear SiNR (S1 design) is used to maximize sensitivity. On the other hand, serpentine SiNR (e.g. S3 or S6 design) is applied on stretchier areas, thus accommodating the larger range of strain changes. Furthermore, the curvature of SiNR is optimally designed depending on the stretchability (e.g. low deformation region of about 5%: S1 design, medium deformation region of about 10%: S3 design, high deformation region of about 16%: S6 design, the right frames of FIG. 3C). Such a site-specific SiNR sensor array is illustrated in FIG. 3D. The exploded frames on the right are enlarged images of individual designs. These ultrathin filamentary designs enable conformal integration on the human skin with high signal sensitivity and mechanical durability.

SiNR Mechanical Sensor Having Site-Specific Sensitivity (Strain Gauge and Pressure Sensor)

Figure 5A:
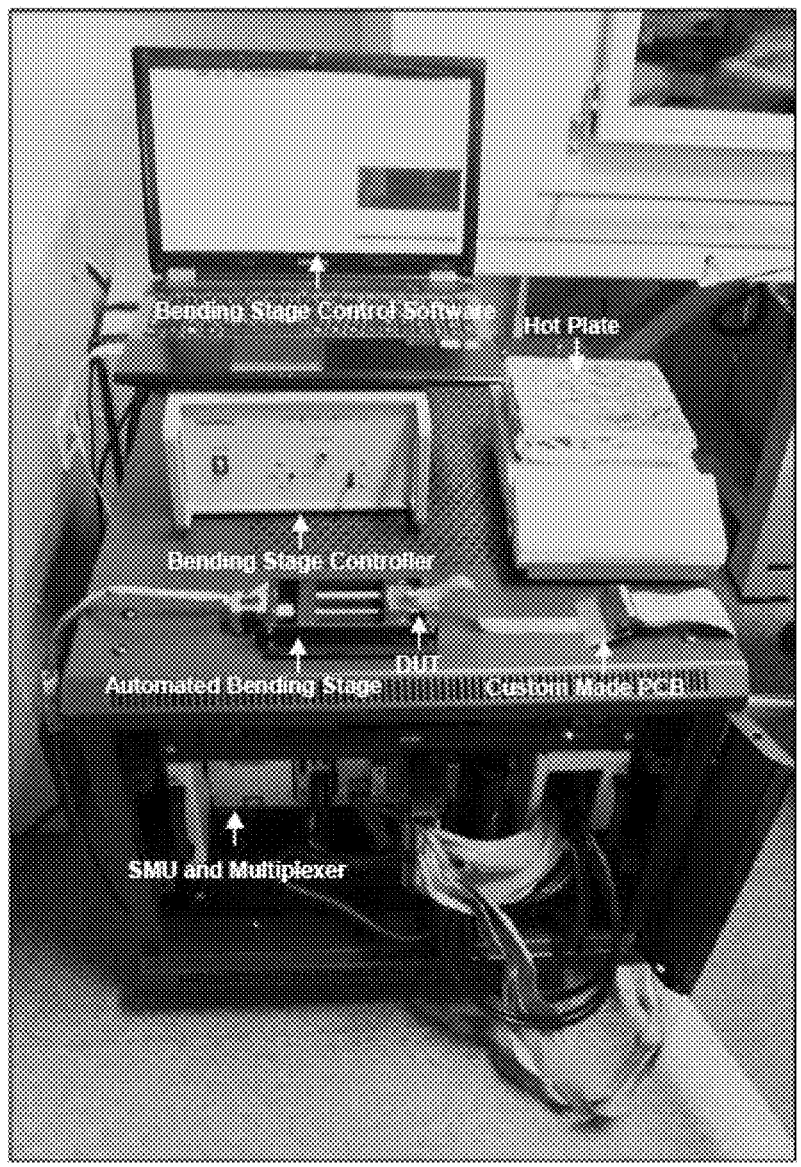
FIG. 5A illustrates the experimental setup for measuring the strain and temperature using the SiNR-based sensor array.
Figure 6A:
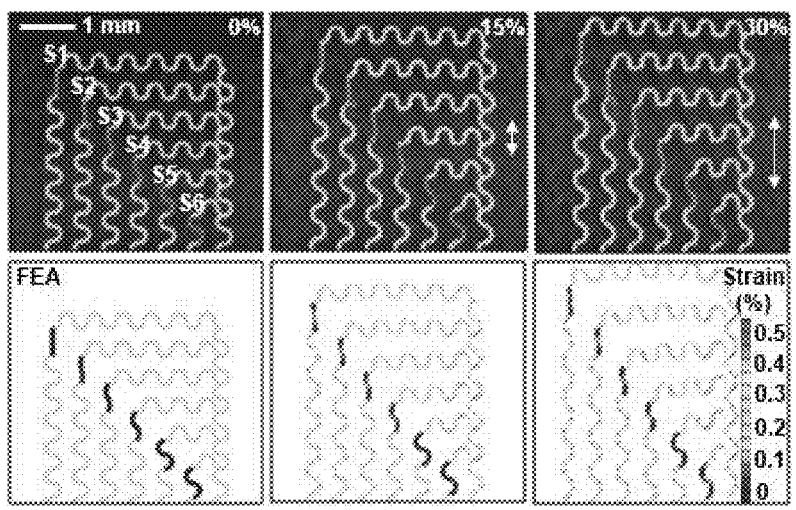
FIG. 6A illustrates the sequential images (on the top) of the SiNR strain gauges under differently applied strains (0, 15 and 30%), and the corresponding finite element analysis (FEA) results (on the bottom)

To characterize the effects of strain on different SiNR sensor designs, there are provided six unique serpentine designs having curvatures of κ=0 (S1), 1.94 (S2), 4.74 (S3), 7.4 (S4), 9.75 (S5) and 10 mm$^{-1}$ (S6). The stretching experimental setup using a bending stage is illustrated in FIG. 5A. FIG. 6A (on the top frames) shows the SiNR strain gauge array exposed to a variety of applied strains (0, 15 and 30%). The bottom frames show the results of finite element analysis (FEA). As the applied strain increases, the SiNR strain gauge, having a small curvature, experiences significantly great strain compared to those having larger curvatures. The serpentine designs having large curvatures may more efficiently relieve induced strain than smaller ones. This effect can be determined by measuring relative resistance ($\Delta$ R/R) as a function of applied strain (on the left of FIG. 6B).

Figure 6B:
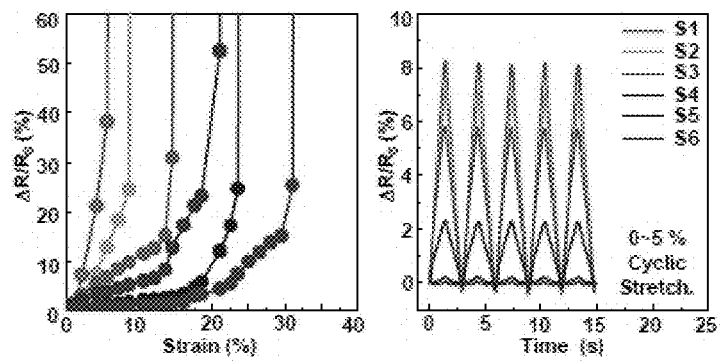
FIG. 6B illustrates changes in resistance (on the left) for SiNR having different curvatures depending on the strain applied thereto, and changes in resistance over time for SiNR having different curvatures under repeated stretching.
Figure 7A:
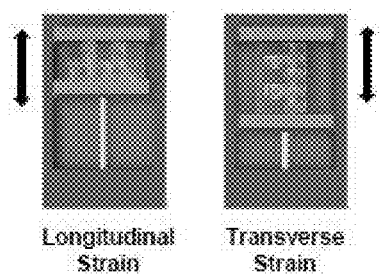
FIG. 7A illustrates the experimental setup for analyzing the dependency of the SiNR strain gauge on the stretched direction.
Figure 7B:
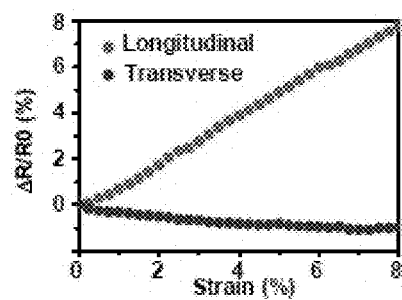
FIG. 7B illustrates the percent resistance changes of the SiNR strain gauge to strain in the vertical direction (red) and the horizontal direction (blue)
Figure 7C:
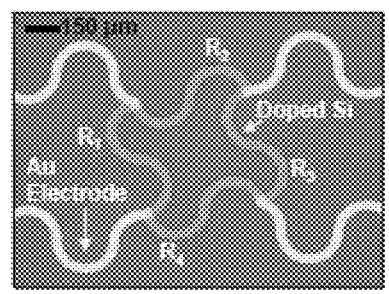
FIG. 7C illustrates the microscope image of the SiNR strain gauge in a Wheatstone bridge configuration.
Figure 7D:
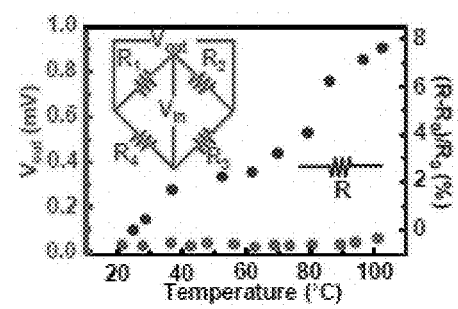
FIG. 7D illustrates the output voltage changes (red) measured from the Wheatstone bridge and the percent resistance changes (blue) of the single-resistor-based strain gauge, represented by the temperature function (wherein the red inset shows the Wheatstone bridge and the blue inset shows the single resistor)

The SiNR sensor having a larger curvature may withstand greater applied strain, and thereby may have a large dynamic range, but exhibits reduced sensitivity (FIG. 6B). SiNR S6 sustains strain up to about 30%, whereas SiNR S1 fractures at strain levels of about 10% applied thereto. However, repeated stretching testing reveals that sensitivity increases with a decrease in the curvature (on the right of FIG. 6B). Accordingly, SiNR S1 is most appropriate for sites with a small range of stretching, whereas SiNR S6 is more suitable for sites that experience large stretching. The results also indicate that the SiNR strain gauge has a linear and fast response time and no hysteresis, regardless of the design. When S1 and S6 strain gauge arrays are combined, anisotropic stretching over the regions may be accommodated (FIGS. 7A and 7B). The noise in the strain sensor is often caused by changes in external temperature, which affects individual strain sensor resistance measurements. To reduce the effects of noise caused by such thermal shift, a Wheatstone bridge configuration may be applied (FIGS. 7C and 7D).

Figure 5B:
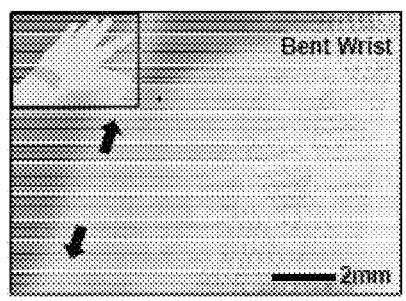
FIG. 5B is an enlarged image illustrating the strain gauge array conformally attached to the wrist.
Figure 5C:
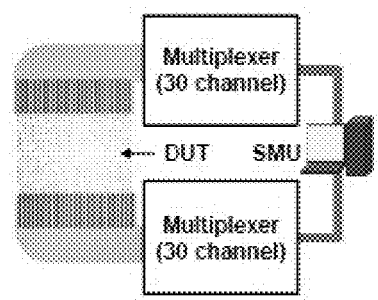
FIG. 5C illustrates the multiplexer for measuring strain distributions at different positions using the sensor array.
Figure 6C:
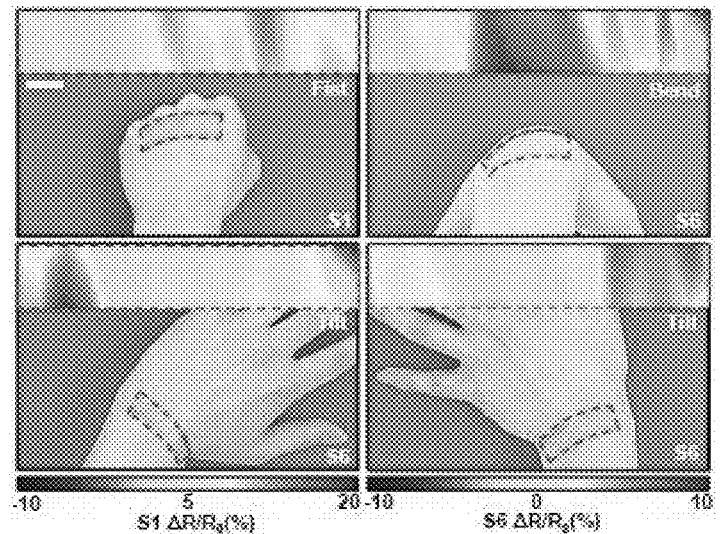
FIG. 6C illustrates regionally mapped percent resistance changes, measured using the strain gauge array (S1 for a small stretch region and S6 for a large stretch region), wherein the mapped regions are indicated with red dotted-line boxes for four different motions.
Figure 8A:
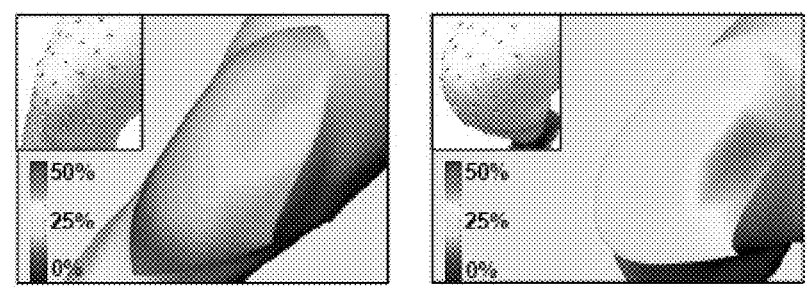
Figure 8B:
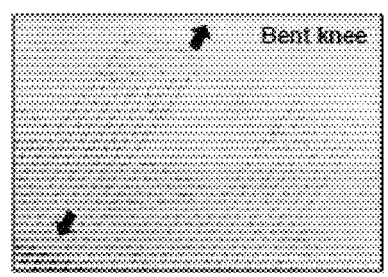
Figure 8C:
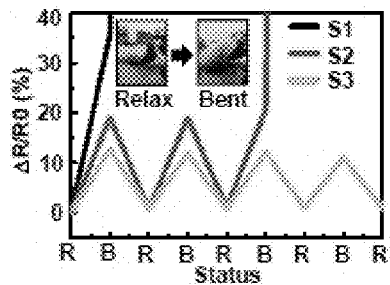
Figure 9A:
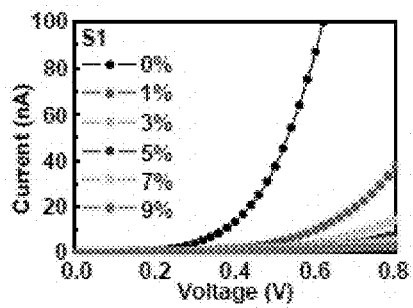
FIGS. 9A to 9F illustrate the I-V curves of the temperature sensor in the presence of strain (0%, 1%, 3%, 5%, 7%, 9%) for different designs (FIG. 9A: S1, FIG. 9B: S2, FIG. 9C: S3, FIG. 9D: S4, FIG. 9E: S5, FIG. 9F: S6) at room temperature.
Figure 9B:
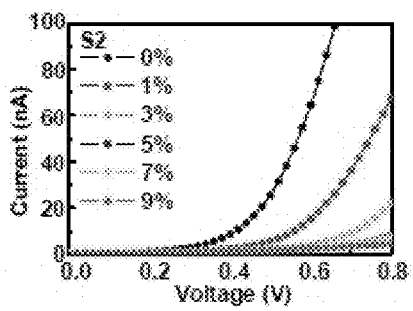
Figure 9C:
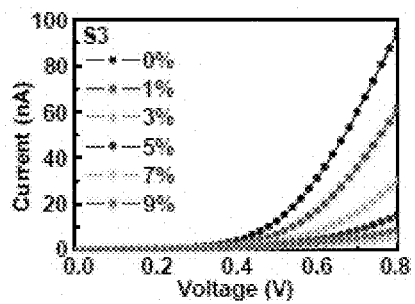
Figure 9D:
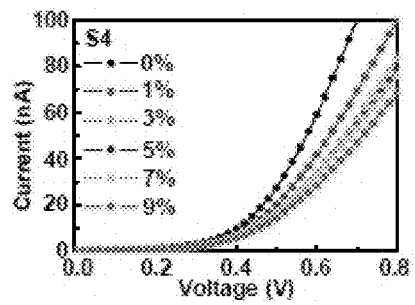
Figure 9E:
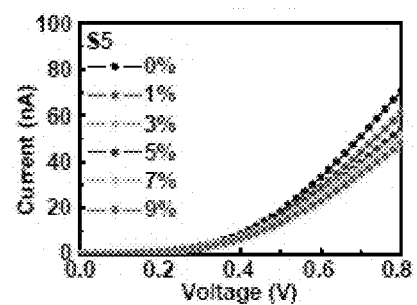
Figure 9F:
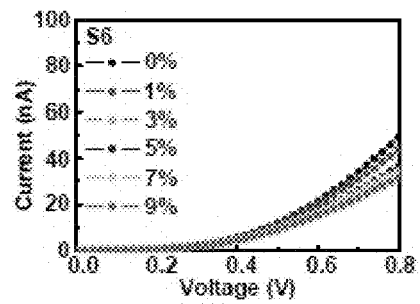

Site-specific designs for strain gauge arrays that conform to the complex geometry of the human hand (FIGS. 3D and 5B) are used to measure the strain distribution. FIG. 6C shows strain distribution maps (red dotted-line box regions) in response to four representative hand motions. The signals are collected using a multiplexing measurement unit (FIGS. 5A and 5C). For locations where skin deformations are small (e.g. the back of hand), the S1 design is used (fist clenching: on the top left of FIG. 6C). Despite small strain induced on the back of the hand, the SiNR strain gauge array having the S1 design successfully maps the regional strain distribution. In contrast, the SiNR strain gauge array having the S6 design is used in locations where large skin deformations occur (wrist region: on the top right and the bottom of FIG. 3B), with significant bending (on the top right of FIG. 6C) and tilting (on the bottom of FIG. 6C). The SiNR strain gauge array may measure induced large strain with high fidelity. Even larger induced strains near the knee may be measured (FIGS. 8A and 8B). The SiNR strain gauge having a large curvature (e.g. S3) may endure mechanical deformation in response to repeated bending of the knee joints better than one having a small curvature (e.g. S1) (FIG. 8C).

Figure 6D:
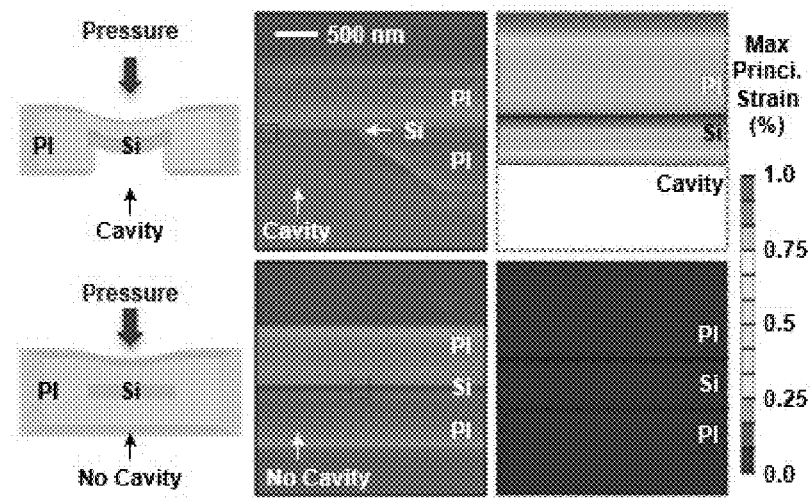
FIG. 6D illustrates the operating principle of the SiNR pressure sensor having a cavity compared to the SiNR pressure sensor lacking a cavity (on the bottom left), SEM images of the cross-section of the device having a cavity (on the top middle) and the cross-section of the device lacking a cavity (on the bottom middle), and FEA results (on the top right and the bottom right)
Figure 6E:
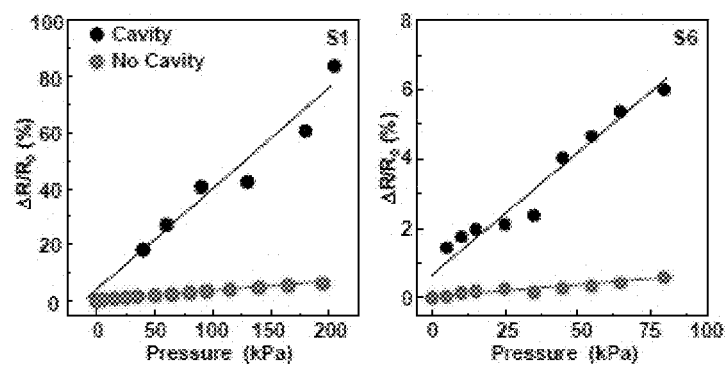
FIG. 6E illustrates changes in the resistance of a pressure sensor having a cavity (black) and a pressure sensor lacking a cavity (red) with respect to the applied pressure for different SiNR designs (S1: graph on the left, S6: graph on the right)
Figure 6F:
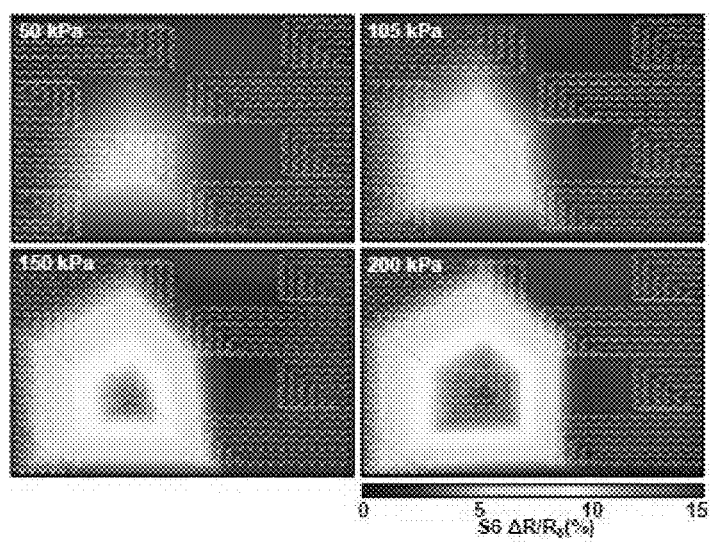
FIG. 6F illustrates regionally mapped percent resistance changes measured by the pressure sensor array of S6 with a gradual increase in pressure.

FIG. 6D shows the operating principle of the SiNR pressure sensor. By designing a cavity in the PI passivation layer of SiNR, the pressure detection sensitivity is enhanced, as was confirmed by FEA (on the top versus the bottom of FIG. 6D). For S1 and S6 designs, the cavity-based SiNR pressure sensor shows sensitivity to applied pressure about 10 times higher than the SiNR pressure sensor lacking the cavity (FIG. 6E). The detailed measurements of sensitivity for S1 and S6 are 0.41% kPa$^{-1}$ (having a cavity) versus 0.0315% kPa$^{-1}$ (lacking a cavity) and 0.075% kPa$^{-1}$ (having a cavity) versus 0.0073% kPa$^{-1}$ (lacking a cavity), respectively. The serpentine-shaped SiNR pressure sensor (e.g. S6) has reduced sensitivity to vertical pressure, compared to the linear pressure sensor (S1). However, the pressure sensitivity of the S6 design sensor is comparable to human mechanoreceptor responses, which respond to stress as low as about 87 kPa. FIG. 6F illustrates the pressure response maps from the sensor array in the S6 design.

SiNR Temperature Sensor, Humidity Sensor and Heater

Figure 1D:
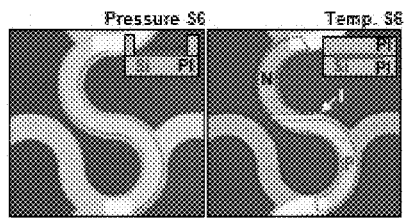
FIG. 1D illustrates representative microscope images of the SiNR pressure sensor S6 and the temperature sensor S6.
Figure 1E:
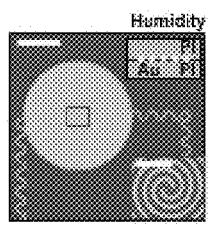
FIG. 1E illustrates a microscope image of the humidity sensor (in which the bottom right inset shows an enlarged view of the central area, showing individual electrodes having an identical inter-spiral gap)
Figure 1F:
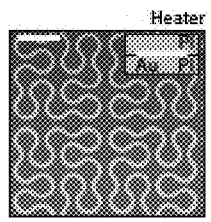
FIG. 1F illustrates a microscope image of the electroresistive heater, wherein the top right insets of FIGS. 1C to 1F are cross-sectional views illustrating respective devices.
Figure 1G:
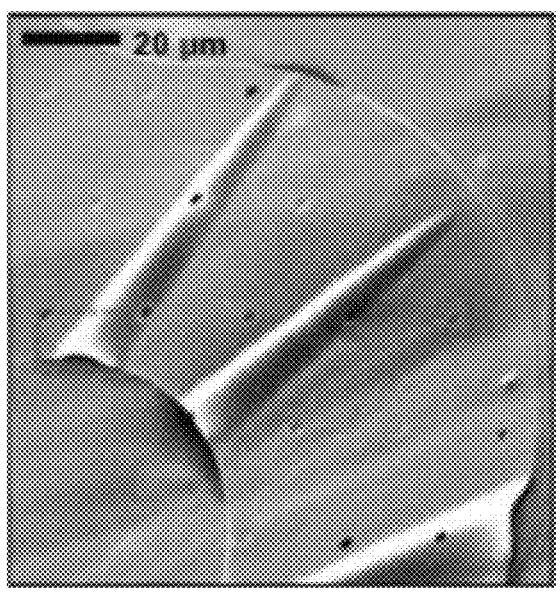
FIG. 1G is a scanning electron microscope (SEM) image of SiNR transferred onto the silicon oxide substrate.
Figure 1H:
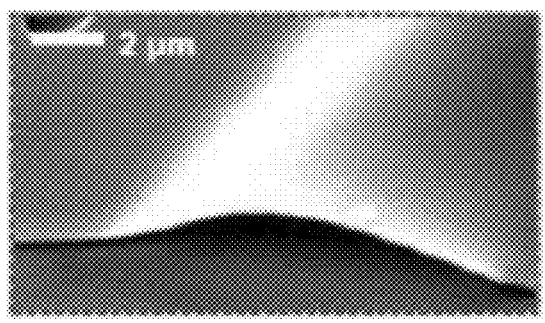
FIG. 1H is an enlarged view illustrating the wrinkled SiNR of FIG. 1G.
Figure 1I:
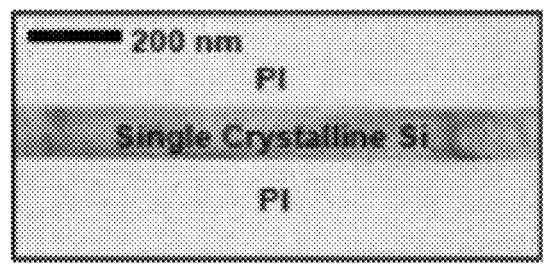
FIG. 1I illustrates a cross-sectional transmission electron microscope (TEM) of the strain gauge, showing that the SiNR encapsulated with polyimide (PI) layers is located in the neutral mechanical plane.
Figure 2A:
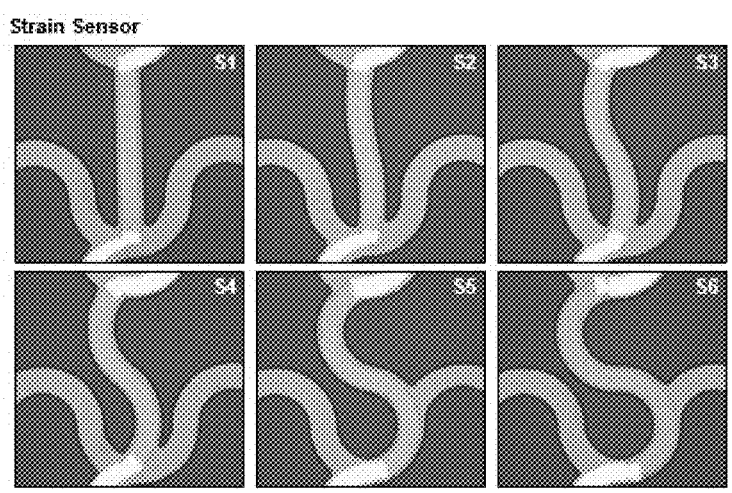
FIGS. 2A and 2B illustrate microscope images of the strain and temperature sensors in serpentine form having various curvatures of κ=0 (S1), 1.94 (S2), 4.74 (S3), 7.4 (S4), 9.75 (S5) and 10 mm$^{-1}$ (S6), FIG. 2A showing the p-type doped SiNR in linear and serpentine form for the strain sensor, FIG. 2B showing the SiNR p-n junction diode in linear and serpentine form for the temperature sensor.
Figure 2B:
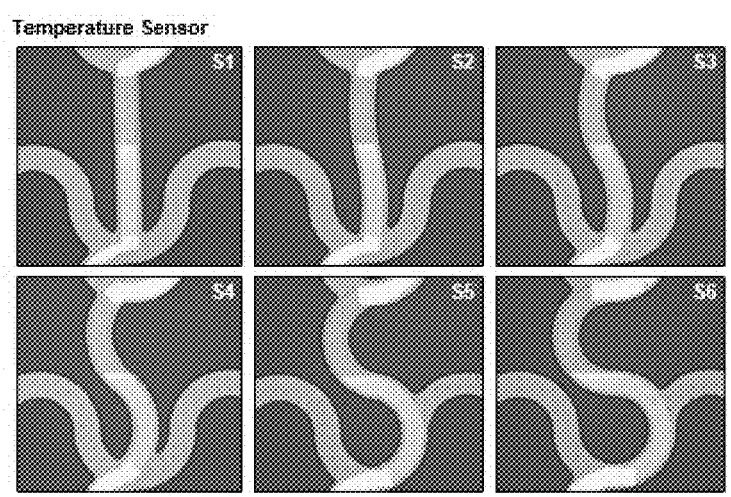
Figure 10A:
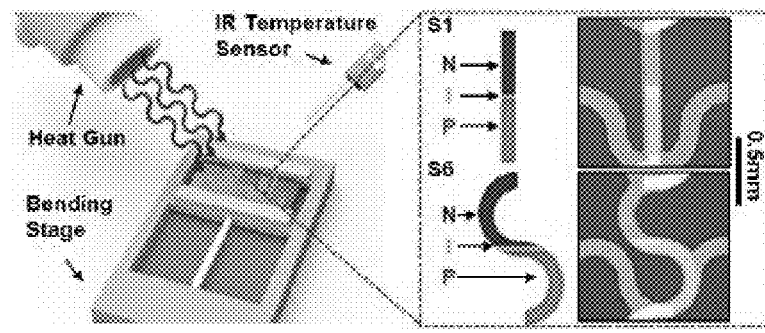
FIG. 10A illustrates the schematic experimental setup for evaluating the characteristics of the SiNR temperature sensor.
Figure 10B:
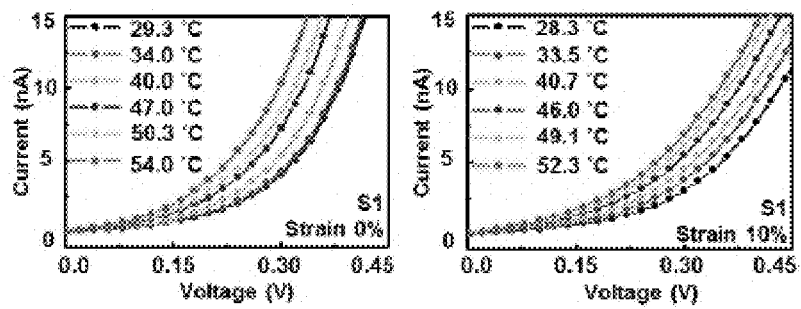
FIG. 10B illustrates the I-V curves of the S1 temperature sensor in the absence of strain (on the left) and in the presence of strain (on the right, 10%)
Figure 10C:
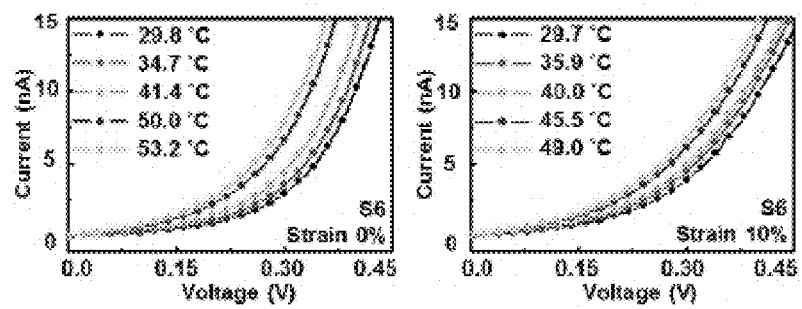
FIG. 10C illustrates the I-V curves of the S6 temperature sensor in the absence of strain (on the left) and in the presence of strain (on the right, 10%)
Figure 11A:
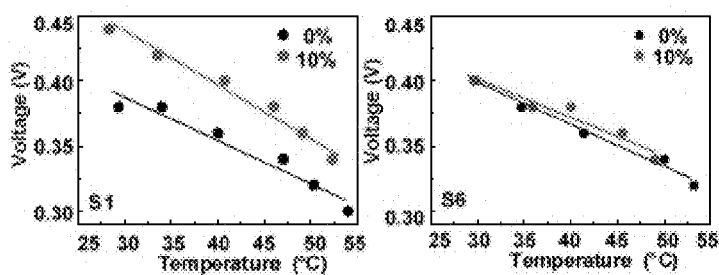
FIG. 11A illustrates calibration curves of the SiNR temperature sensor for representative designs (S1: graph on the left and S6: graph on the right) in the presence of 10% strain (red) and in the absence of strain (black)
Figure 11B:
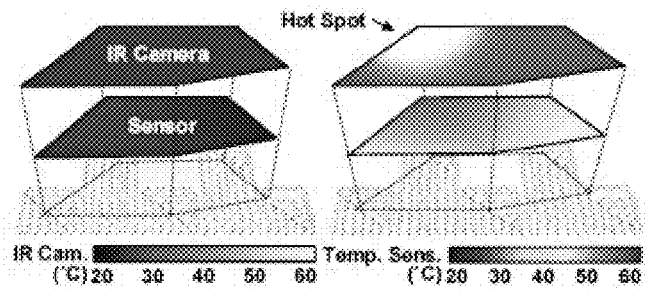
FIG. 11B illustrates the regionally mapped temperature measured by an IR camera and the SiNR temperature sensor array in S6 design under an initial condition (on the left) and a partially heated condition (on the right)

To measure temperature, SiNR is doped twice to form a p-n junction (on the right of FIG. 1D). The temperature sensors integrated with the artificial skin must not be affected by mechanical deformation. FIGS. 9A to 9F show I-V curves of the temperature sensors (S1 to S6 designs) at room temperature in response to strains applied thereto. The divergence between the I-V curves under different strains is remarkably reduced as the curvature of the sensors is increased (e.g. S6). The large curvature of the sensors allows for stable temperature measurements under a wide range of stretching conditions. The I-V curves of the S1 and S6 temperature sensors are obtained at different temperatures under 0% and 10% applied strains (FIGS. 10A to 10C). FIG. 11A illustrates the calibration curves obtained by extracting voltage at specific current (about 10 nA) from the I-V curves. The calibration curves for the S1 design show a drastic shift in response to strain applied thereto, whereas the S6 design exhibits minimal change. The temperature sensor in the S6 design is used to minimize the effect of mechanical deformation on the temperature sensing. The temperature sensor design having a large curvature enables temperature monitoring under variously applied pressures. The temperature distribution map is realized with these sensor arrays, with and without local heating (on the left and the right of FIG. 11B). The temperature sensor array data streams are comparable to those collected using a commercially available IR camera. The spatial resolution of the temperature sensor array of SiNR diodes is sufficiently high to accurately recognize the thermal profile of a heated object.

Figure 11C:
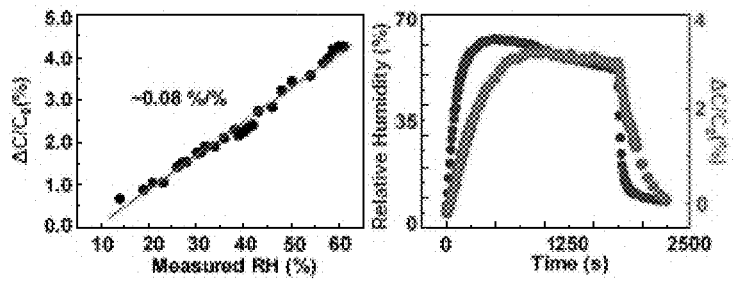
FIG. 11C illustrates the calibration curve of the coplanar humidity sensor (on the left) and the double y-plot of the simultaneously measured changes in humidity and capacitance of the coplanar humidity sensor over time.
Figure 11D:
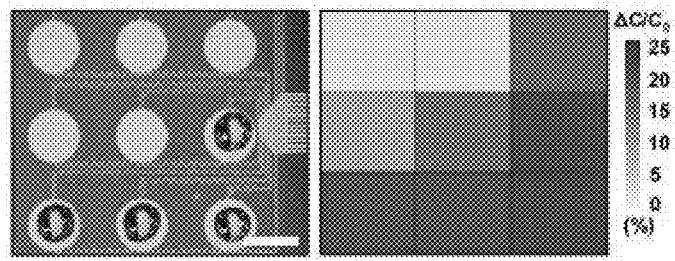
FIG. 11D is an image of water droplets covering the partial area of the coplanar humidity sensor array (on the left) and the corresponding map of regional capacitance changes (on the right)
Figure 12A:
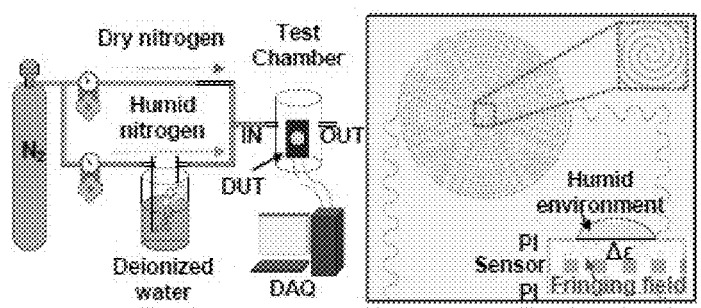
FIG. 12A illustrates the experimental setup (on the left) for the humidity sensor according to the present invention, and the schematic diagram (on the right) for the sensor and the sensing mechanism.
Figure 12B:
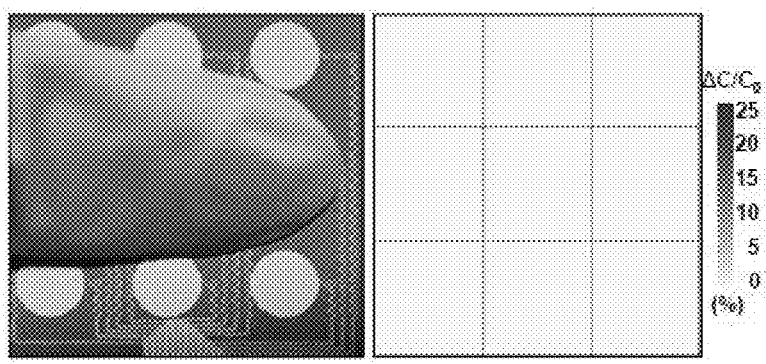
FIG. 12B illustrates the external disorder test (on the left) in which a dry fingertip comes into contact with the humidity sensor array, and the response (on the right) of the humidity sensor corresponding thereto.

Although there is no specific biological receptor that senses the exposure of skin to humidity, human skin has the ability to sense changes in humidity using mechanoreceptors and thermoreceptors. To mimic this capability, stretchable capacitance-based humidity sensor arrays are manufactured. Humidity sensing is performed in a test chamber that controls humidity (on the left of FIG. 12A). The humidity sensor arrays detect changes in capacitance induced by changes in the permittivity of PI, into which water molecules are absorbed (on the right of FIG. 12A). The calibration curve (on the left of FIG. 11C) demonstrates this behavior. The right frame of FIG. 11C shows that changes in the relative humidity, measured using a commercially available humidity sensor (blue), are highly correlated with changes in the capacitance measured using the manufactured humidity sensor (red). Spatial differences in humidity are distinguished (FIG. 11D). External disturbances, such as fingertip touch, external strain, and temperature changes have negligible effects on the humidity sensing (FIG. 12B).

Figure 11E:
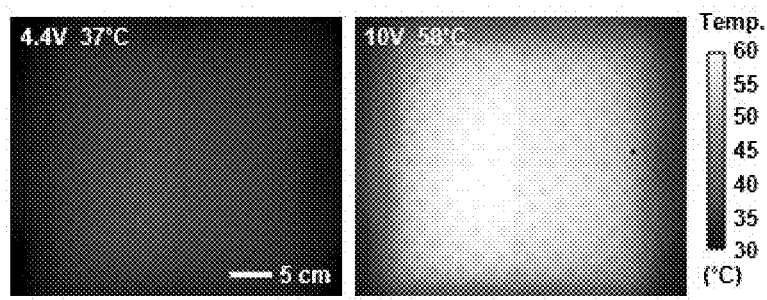
FIG. 11E illustrates the heating capability of the heater (a fractal-inspired stretchable heater at 37° C. for emulating body temperature (on the left) and heated to 58° C. (on the right))
Figure 11F:
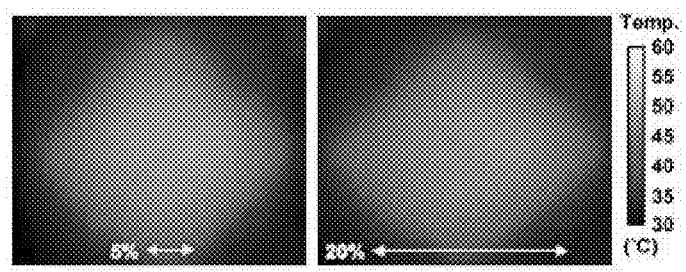
FIG. 11F illustrates the stretchability of the heater (wherein the heater is stretched from about 5% (on the left) to about 20% (on the right), without degradation in heating performance)

In order for the prosthetic device and artificial skin to feel natural, the temperature profile thereof must be controlled to match that of the human body. Thus, a stretchable thermal actuator array, the thermal signals of which are easily controllable, is manufactured. The heater array may maintain the body temperature (on the left of in FIG. 11E), or may be adjusted to higher temperatures (on the right of FIG. 11E). The performance of the thermal actuator remains intact under various stretching conditions (about 5% and about 20%; FIG. 11F).

Electronic Skin Response in Various Daily Life Situations

Figure 13A:
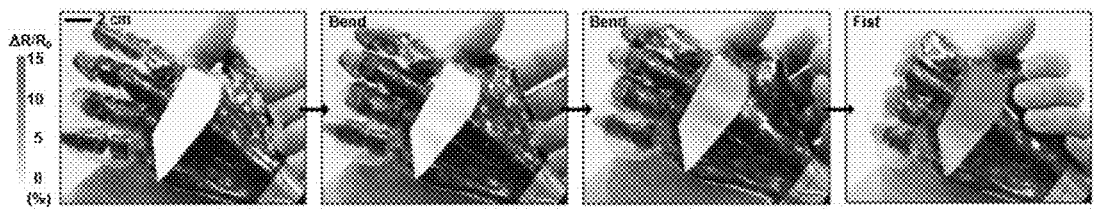
FIG. 13A illustrates sequential images of a prosthetic hand performing a handshake (wherein the spatiotemporal maps of changes in the resistance of the SiNR strain gauge overlap each other at corresponding locations on the back of the hand)
Figure 13B:
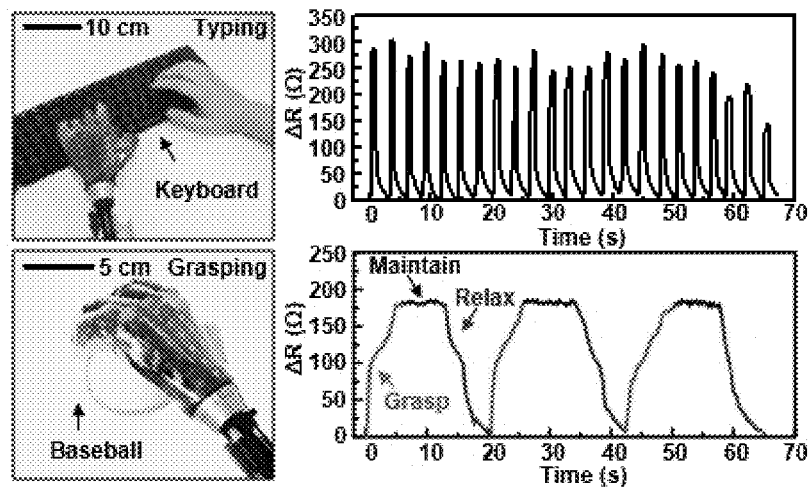
FIG. 13B illustrates an image of the prosthetic hand tapping a keyboard (on the top left), the changes in resistance over time of the SiNR pressure sensor corresponding thereto (on the top right), an image of the prosthetic hand grasping a baseball (on the bottom left), and the changes in resistance over time of the SiNR pressure sensor corresponding thereto (on the bottom right) (showing dynamics of the prosthetic hand in grasping motion (red), maintaining motion (black) and relaxing motion (blue))
Figure 13C:
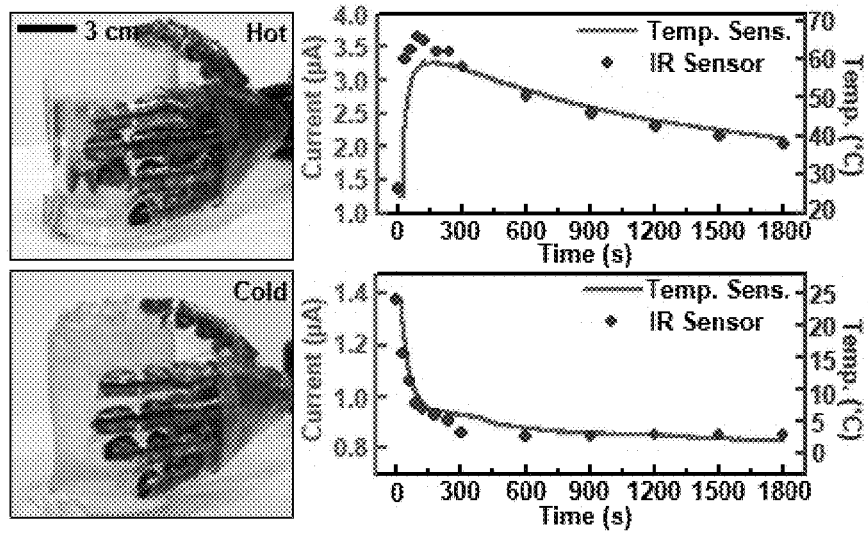
FIG. 13C illustrates images of the prosthetic hands touching a hot cup (on the top left) and an ice water cup (on the bottom left), and plots for the changes (PIN diode, red) in the current over time of the SiNR temperature sensor corresponding thereto, and the changes (blue) in the actual temperature measured using the IR sensor (hot water on the top right, and ice water on the bottom right)
Figure 13D:
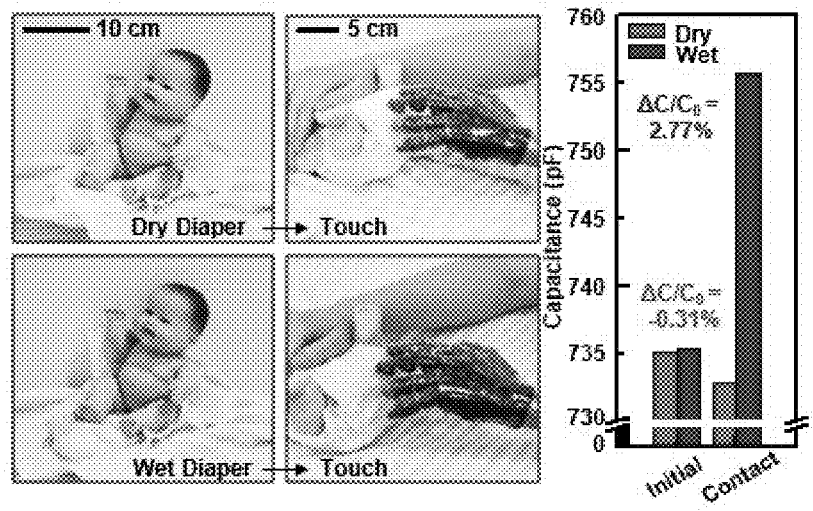
FIG. 13D illustrates images of baby dolls with a dry diaper (on the top left) and a wet diaper (on the bottom left), and of prosthetic hands touching the dry diaper (on the top middle) and the wet diaper (on the bottom middle), and a bar plot (on the right) of the capacitance value of the humidity sensor before/after touching the dry (red)/wet (blue) diaper.
Figure 13E:
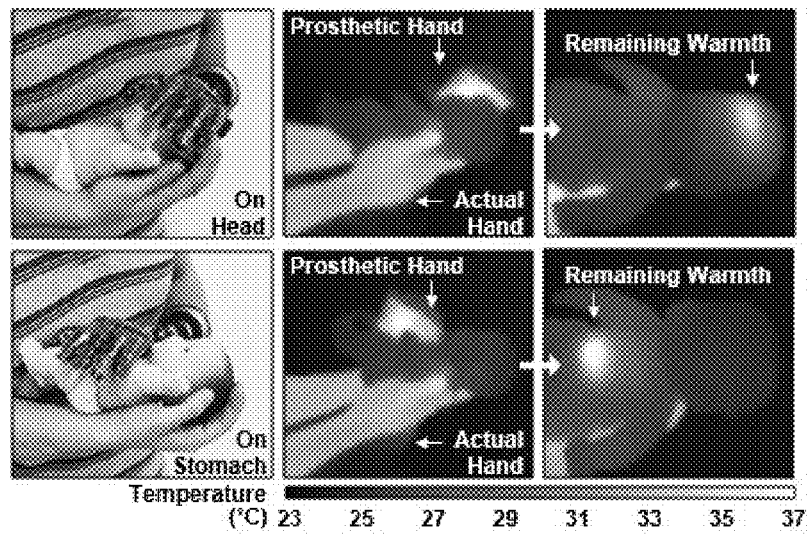
FIG. 13E illustrates images of the prosthetic hands touching the head of the baby doll (on the top left) and the stomach of the baby doll (on the bottom left), IR camera images of the prosthetic hand heated to the body temperature by the heater in the artificial skin (on the top middle and the bottom middle), and images of the heat remaining on the baby doll after removing the prosthetic hand (on the top right and the bottom right)

The prosthetic hand and the laminated electronic skin may encounter many complex operations, such as hand shaking, keyboard tapping, ball grasping, holding a cup of hot/cold beverage, touching dry/wet surfaces and human-to-human contact (FIGS. 13A to 13E). In the case of hand shaking, spatiotemporal strain can be mapped using SiNR strain gauge arrays. The strain map has high fidelity and captures minor shifts in strain near the index finger and respective joints (FIG. 13A). To investigate the performance of the SiNR pressure sensor, changes in resistance over time in response to keyboard tapping (on the top of FIG. 13B) and ball grasping (on the bottom of FIG. 13B) are monitored. The pressure sensor shows rapid and reliable responses to external stimuli in both situations. Temperature sensing is another important function of the artificial skin. Temporal temperature monitoring is evaluated to be successful (red) when a hand touches a cup containing a hot (on the top of FIG. 13C) or cold (on the bottom of FIG. 13C) liquid. The control temperature is measured using an IR sensor (blue).

Another application of the artificial skin is sensing of dampness caused by fluid contact. The humidity sensor in the artificial skin provides feedback on the levels of humidity and wetness (on the top and the bottom of FIG. 13D, respectively) of a diaper. The measured capacitance differences between the dry and wet cases are clearly distinguishable (on the right of FIG. 13D). In addition, the thermal actuator may provide controlled heating that makes the sense of touch from the artificial skin feel close to natural (on the left of FIG. 13E). The artificial skin having the stretchable heater is warmed to about 36.5° C. to mimic the body temperature. The heat transfer to the baby doll is then captured using an IR camera (on the right of FIG. 13E).

Synthesis of PtNWs (Platinum Nanowires) on Au Electrode

A 1% (w/w) $H_2PtCl_6$ (≥99.5%) solution containing 1.5 M $HClO_4$ (70%) is prepared for electrodeposition. A porous anodic aluminum oxide (AAO) template is laminated onto the Au electrode array and immersed in the $H_2PtCl_6$ solution. A holder firmly fixes the AAO template on the Au electrode. Electrodeposition is performed using an electrochemical workstation having the three-electrode system: Pt, Ag/AgCl and Au electrode as a counter electrode, reference electrode and working electrode, respectively. In the potentiostatic mode at a potential of −0.35 V, electrodeposition is carried out for about 30 min at room temperature. After completion of the electrodeposition, the sample is washed with triple-distilled water. Finally, the sample is immersed in a 1 M NaOH solution at room temperature for about 30 min to dissolve the AAO template.

Synthesis of Ceria Nanoparticles 1 mmol (0.4 g) of cerium (III) acetate (98%) and 12 mmol (3.2 g) of oleylamine (about 80 to 90% of C18) are added to 15 ml of xylene (98.5%). The mixed solution is treated using a sonicator for about 15 min at room temperature and then heated to 90° C. 1 ml of deionized water is injected into the solution with vigorous stirring at 90° C., and then the color of the solution turns to off-white, indicating that the reaction has occurred. The resulting mixture is aged at 90° C. for 3 hr to give a light yellow colloidal solution, which is then cooled to room temperature. Acetone (100 ml) is added to the precipitated ceria nanoparticles. The precipitate is washed with acetone using centrifugation and the resulting ceria nanoparticles are easily dispersible in chloroform.

Synthesis of Phospholipid-PEG-Capped Ceria Nanoparticles

To prepare biocompatible ceria nanoparticles, ceria nanoparticles dispersed in chloroform are encapsulated by polyethylene glycol (PEG)-phospholipid shells. Specifically, 5 ml (10 mg/ml) of ceria nanoparticles in $CHCl_3$ are mixed with 35 ml of a $CHCl_3$ solution containing 30 mg of mPEG-2000 PE. Then, the solvent is evaporated by a rotary evaporator, followed by incubation at 70° C. in vacuum for 1 hr to completely remove the chloroform. 5 ml of water is added, forming a clear and light-yellowish suspension. After filtration, excess mPEG-2000 PE is removed using ultracentrifugation. The purified phospholipid-PEG-capped ceria nanoparticles are dispersed in distilled water.

Anti-Oxidant Properties of Ceria Nanoparticles

To evaluate the anti-oxidant properties of ceria nanoparticles, a catalase mimetic assay is used. Quenching hydrogen peroxide is quantified using an assay kit (Amplex® Red Hydrogen Peroxide/Peroxidase assay kit). Amplex Red reagent (10-acetyl-3,7-dihydroxyphenoxazine) reacts with hydrogen peroxide, thus producing the red fluorescent resorufin with horseradish peroxidase (HRP). The florescence of resorufin (excitation at 571 nm and emission at 585 nm) indicates the hydrogen peroxide ($H_2O_2$) level in the samples. First, an $H_2O_2$ standard curve is prepared for determining the $H_2O_2$ concentration of each sample. After drop casting of 30 μl of a 5 mM ceria nanoparticle solution on the PtNW-coated electrodes, each sample is placed in a micro-well and 50 μl of a $H_2O_2$ solution is added. Subsequently, 50 μl of an Amplex Red reagent/HRP working solution is added. The initial concentration of $H_2O_2$ is 5 μM. The fluorescence is measured after incubation for 30 min at room temperature.

Figure 14A:
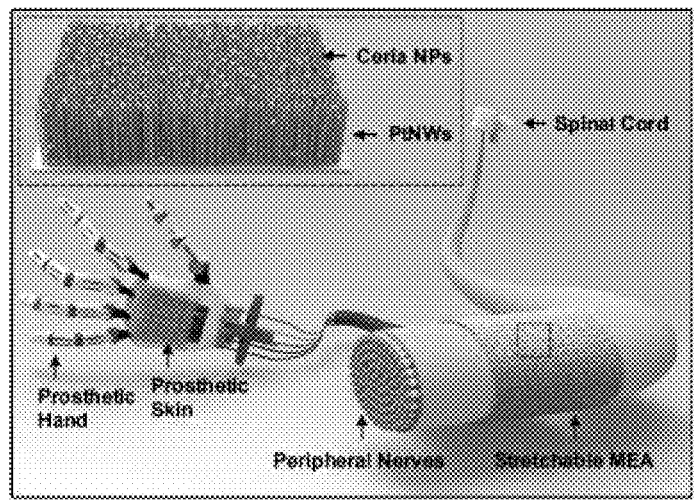
FIG. 14A illustrates the process of interconnecting the prosthetic hand to peripheral nervous fibers using a multi-electrode array (MEA) (in which the inset shows that platinum nanowires (PtNWs) having ceria nanoparticles adsorbed thereto are grown on the gold (Au) electrode)

Transmission of Sensory Signals to Peripheral Nerves Through Stretchable Electrode The ultimate goal of artificial skin is to enable amputees to feel various types of external stimuli. To achieve this goal, the signals captured across various sensor arrays must be processed and transmitted to stimulate the corresponding peripheral nervous system (FIG. 14A). For effective charge injection to peripheral nerves, low impedance of the multi-electrode array (MEA) is regarded as important. In addition, there are various mechanical motions of adjacent muscles, which require deformation of the interfacing electrodes to preserve mechanically conformal contact and prevent scratching due to mechanical mismatch between biological tissues and MEA. Furthermore, inflammation at the interfaces between electrodes and nerves, caused by reactive oxygen species, must be suppressed because massive inflammatory responses may cause death of nervous cells and damage to the peripheral nervous system.

Figure 14B:
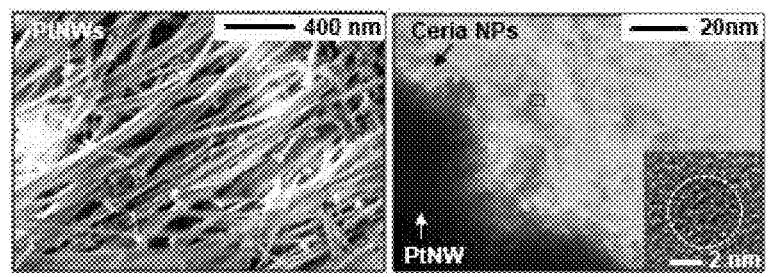
FIG. 14B illustrates the SEM image of PtNWs (on the left) and the TEM image of the ceria nanoparticles adsorbed to PtNWs (on the right)
Figure 14C:
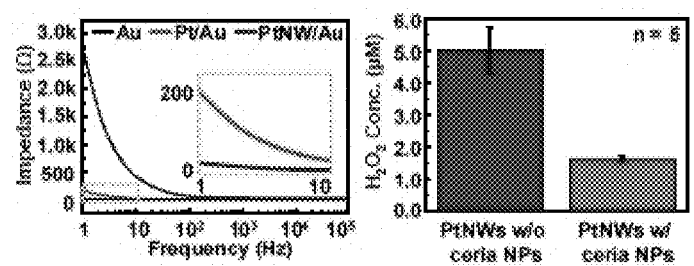
FIG. 14C illustrates the impedance of Au, Pt/Au, PtNWs/Au electrodes at different frequencies of the applied signal (on the left), and ROS scavenging performance comparison between the PtNW/Au electrode with ceria nanoparticles and the PtNW/Au electrode without ceria nanoparticles (on the right)
Figure 14D:
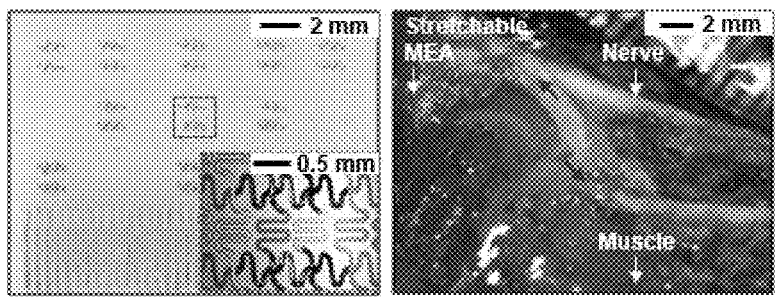
FIG. 14D illustrates images of the stretchable MEA including 34 independent contact electrodes (in which the inset on the left is an enlarged view) and MEA on peripheral nerves in muscle tissues of a rat model (on the right), wherein electrodes that are in contact with nerves are indicated with blue arrows.
Figure 14E:
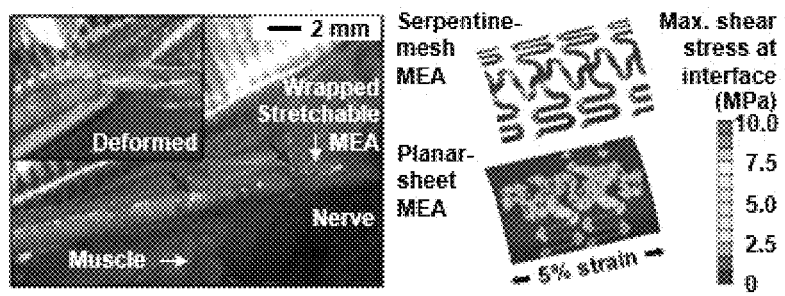
FIG. 14E is an image of stretchable MEA completely wrapped around the nerve fibers of a rat model (on the left; the inset shows that the stretchable MEA maintains conformal contact under deformation of the nerve fibers; and the blue arrows indicate electrodes in contact with nerves), and FEA results (on the right), showing that serpentine-mesh type MEA has lower shear stress than planar-sheet type MEA.
Figure 15A:
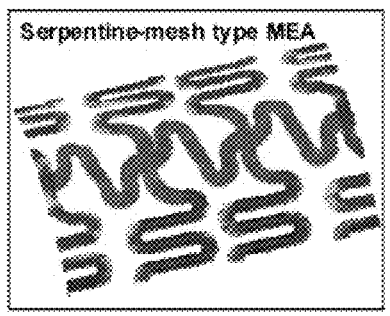
FIGS. 15A and 15B illustrate MEA meshes for the metal interconnection for the serpentine-mesh type MEA and the planar-sheet type MEA, respectively.
Figure 15B:
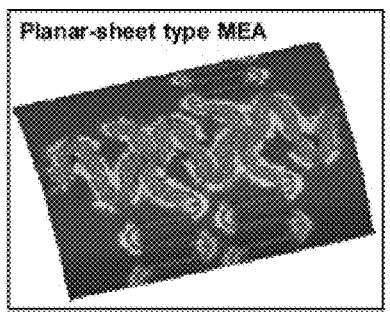

To achieve low impedance, the MEA is coated with PtNWs (the inset of FIG. 14A and on the left of FIG. 14*b*). The PtNWs are grown through an electrochemical method using an anodic aluminum oxide (AAO) nanostructure as a template. The ceria nanoparticles are adsorbed on the PtNWs (on the right of FIG. 14B) to suppress the production of reactive oxygen species, which are neurotoxic at high concentrations. The low impedance of Pt and the large surface area of the nanowires decrease impedance much more than planar Au or Pt electrodes (on the left of FIG. 14C). The ceria nanoparticles applied on the PtNWs successfully scavenge reactive oxygen species (on the right of FIG. 14C), thereby preventing inflammation from being caused by the reactive oxygen species. FIG. 14D illustrates the stretchable MEA (on the left) in conformal contact with nerves (blue arrows) in muscle tissue (on the right). In a Sprague Dawley rat, the sciatic nerve is exposed for the present experiment after the gluteus muscles are dissected. The stretchable MEA is wrapped around the nerve fibers (on the left of FIG. 14E) and maintains conformal contact when deformed (the inset of FIG. 14E). The FEA (on the right of FIG. 14E) shows that much lower shear stress is applied to the nerve fibers when using the stretchable, serpentine-mesh type MEA (on the top right of FIG. 14E) than when using the flexible, planar-sheet type MEA (on the bottom right of FIG. 14E). The MEA meshes for the metal interconnections are illustrated in FIGS. 15A and 15B. The mechanical-stress-induced inflammation may be prevented by virtue of the ceria nanoparticles adsorbed on the stretchable MEA.

Figure 14F:
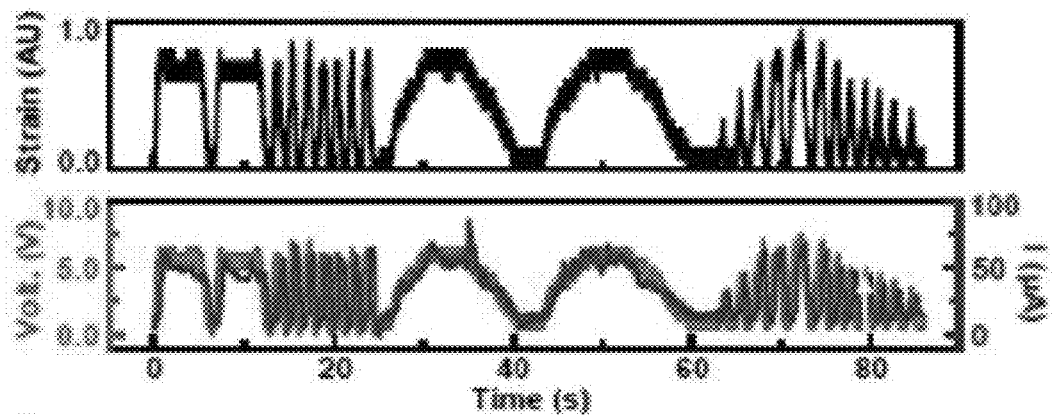
FIG. 14F illustrates the signal (black) measured from the strain gauge provided in the artificial skin, the electrical stimulation (red) applied to nerves in response to the signal sensed in coincidence therewith, and the signal (blue) transferred through the nerves.
Figure 14G:
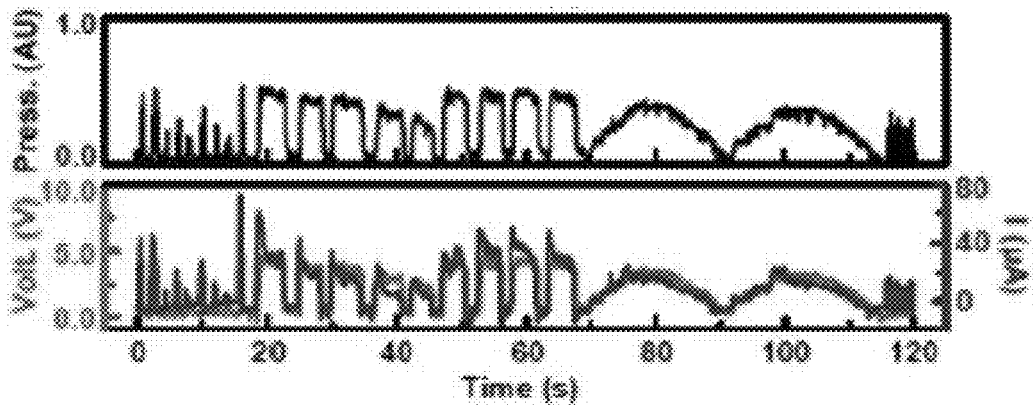
FIG. 14G illustrates data, similar to that of FIG. 14F, obtained using a pressure sensor in the artificial skin.
Figure 16A:
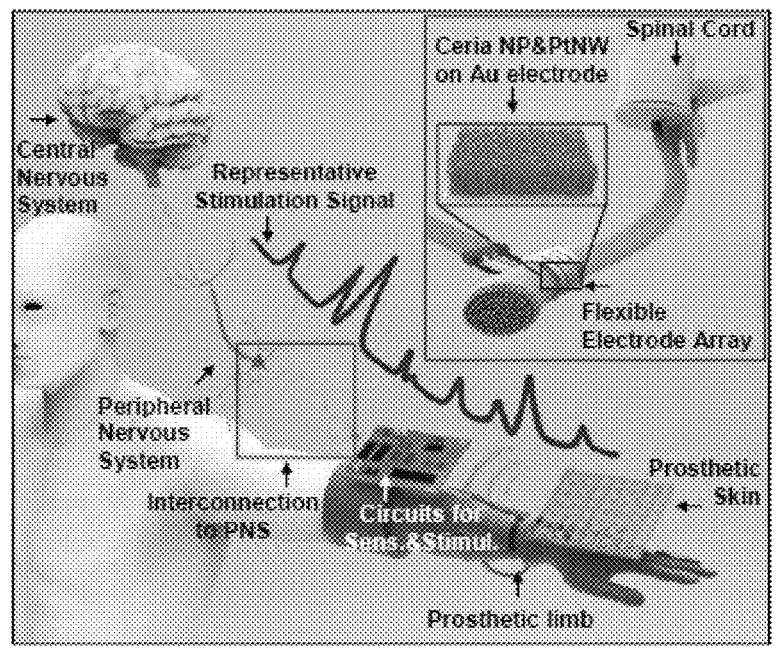
FIG. 16A illustrates elements necessary for manufacturing nervous interfaces for transferring sensed information to the nervous system.
Figure 16B:
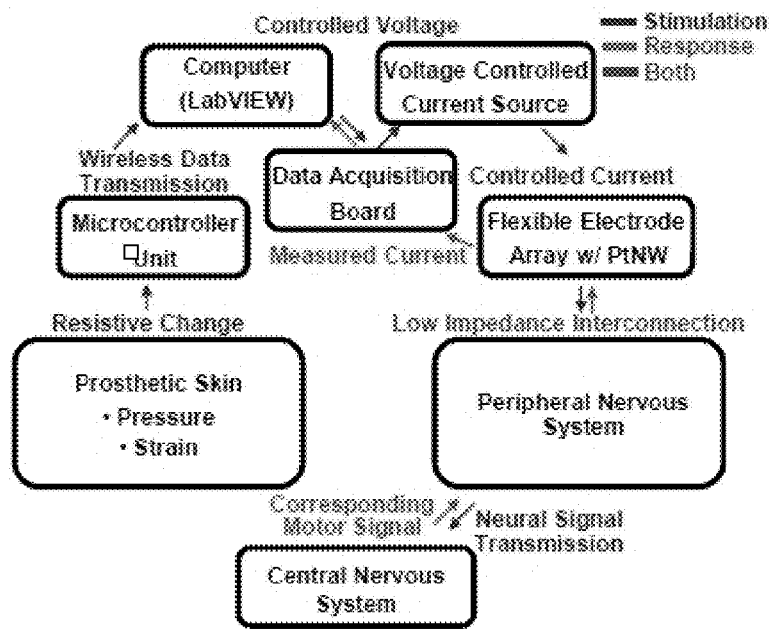
FIG. 16B is a flowchart illustrating the bidirectional feedback concept (wherein the blue arrows, red arrows and violet description respectively correspond to stimulation, response to the stimulation, and both stimulation and response).

System elements and signal flows necessary for nerve stimulation are illustrated in FIGS. 16A and 16B. The signals (black) from strain and pressure sensors are obtained and processed as input signals (red), and are injected to nerves (FIGS. 14F and 14G). The input signals are injected through a stretchable MEA, and the flow of current is measured (blue). The measured signals are similar to the sensor and input signals (FIGS. 14F and 14G), which means that the injection of signals is realized through the stretchable MEA interfaces coated with the nanomaterial.

Although the preferred embodiments of the present invention have been disclosed for illustrative purposes, those skilled in the art will appreciate that various modifications and other equivalent embodiments are possible from the embodiments, without departing from the scope and spirit of the invention as disclosed in the accompanying claims. The disclosed embodiments should be considered to be exemplary rather than restrictive. The scope of the present invention is shown not in the above description but in the claims, and all differences within the range equivalent thereto will be understood to be incorporated in the present invention.

What is claimed is:

1. A stretchable electronic device for artificial skin, comprising:
   a first encapsulation layer;
   a heater disposed on the first encapsulation layer;
   a second encapsulation layer disposed on the heater;
   a first sensor array layer disposed on the second encapsulation layer; and
   a third encapsulation layer disposed on the first sensor array layer;
   wherein the first sensor array layer comprises a first passivation layer, a semiconductor pattern disposed on the first passivation layer, a first metal pattern disposed on the semiconductor pattern, and a second passivation layer disposed on the first metal pattern; and
   wherein the first sensor array layer comprises a pressure sensor, and the pressure sensor has a cavity in the first passivation layer to expose the semiconductor pattern.

2. The stretchable electronic device of claim 1, wherein the first sensor array layer comprises at least one selected from a group consisting of a strain sensor, and a temperature sensor.

3. The stretchable electronic device of claim 1, wherein the semiconductor pattern and the first metal pattern have a serpentine shape.

4. The stretchable electronic device of claim 1, wherein the semiconductor pattern is a silicon pattern formed by patterning a doped silicon nanomembrane.

5. The stretchable electronic device of claim 1, wherein the semiconductor pattern is a silicon nanoribbon.

6. The stretchable electronic device of claim 2, wherein the strain sensor has a Wheatstone bridge configuration.

7. The stretchable electronic device of claim 1, wherein each of the first encapsulation layer, the second encapsulation layer, and the third encapsulation layer is formed of a silicone polymer or silicone rubber.

8. The stretchable electronic device of claim 7, wherein the silicone polymer is polydimethylsiloxane (PDMS).

9. A stretchable electronic device for artificial skin, comprising:
   a first encapsulation layer;
   a heater disposed on the first encapsulation layer;
   a second encapsulation layer disposed on the heater;
   a first sensor array layer disposed on the second encapsulation layer; and a third encapsulation layer disposed on the first sensor array layer, wherein the first sensor array layer comprises a strain sensor and a pressure sensor; and wherein the strain sensor and the pressure sensor have different curvatures depending on a position of a human body to which the stretchable electronic device is attached, and a strain induced by the human body is further relieved with an increase in the curvature.

10. A stretchable electronic device for artificial skin, comprising:

a first encapsulation layer;
a heater disposed on the first encapsulation layer;
a second encapsulation layer disposed on the heater;
a first sensor array layer disposed on the second encapsulation layer; and
a third encapsulation layer disposed on the first sensor array layer,
wherein the first sensor array layer comprises a temperature sensor, and wherein a divergence between I-V curves of the temperature sensor under different strains is decreased with an increase in a curvature of the temperature sensor.

11. A stretchable electronic device for artificial skin, comprising:

a first encapsulation layer;
a heater disposed on the first encapsulation layer;
a second encapsulation layer disposed on the heater;
a first sensor array layer disposed on the second encapsulation layer; and
a third encapsulation layer disposed on the first sensor array layer,
wherein the heater comprises:
a third passivation layer,
a second metal pattern disposed on the third passivation layer, and
a fourth passivation layer disposed on the second metal pattern.

12. The stretchable electronic device of claim 11, wherein the second metal pattern has a serpentine shape.

13. A stretchable electronic device for artificial skin, comprising:

a first encapsulation layer;
a heater disposed on the first encapsulation layer;
a second encapsulation layer disposed on the heater;
a first sensor array layer disposed on the second encapsulation layer;
a third encapsulation layer disposed on the first sensor array layer; and
a second sensor array layer disposed on the third encapsulation layer,
wherein the second sensor array layer comprises a humidity sensor and the humidity sensor detects a change in capacitance induced by a change in permittivity of a sixth passivation layer, into which a water molecule is absorbed.

14. The stretchable electronic device of claim 13, wherein the humidity sensor comprises:

a fifth passivation layer,
a third metal pattern disposed on the fifth passivation layer, and
a sixth passivation layer disposed on the third metal pattern.

15. The stretchable electronic device of claim 14, wherein the third metal pattern has a serpentine shape.

* * * * *